United States Patent
Feng et al.

(10) Patent No.: US 8,757,002 B2
(45) Date of Patent: Jun. 24, 2014

(54) GASBAG TYPE PAVEMENT ACCELERATED LOADING TESTING APPARATUS

(75) Inventors: Jinxiang Feng, Jinan (CN); Xingyu Guo, Jinan (CN); Xuguang Wang, Jinan (CN); Ying Han, Jinan (CN); Peng Zhang, Jinan (CN); Xiangzhen Kong, Jinan (CN); Huijun Wang, Jinan (CN); Xianggui Li, Jinan (CN); Zhiguang Guan, Jinan (CN); Qian Jia, Jinan (CN); Jiwei Zhang, Jinan (CN); Qingzhen Wu, Jinan (CN)

(73) Assignee: Shandong Jiaotong University, Jinan (CN)

( * ) Notice: Subject to any disclaimer, the term of this patent is extended or adjusted under 35 U.S.C. 154(b) by 227 days.

(21) Appl. No.: 13/382,843

(22) PCT Filed: Apr. 29, 2010

(86) PCT No.: PCT/CN2010/072322
§ 371 (c)(1),
(2), (4) Date: Jan. 6, 2012

(87) PCT Pub. No.: WO2011/017943
PCT Pub. Date: Feb. 17, 2011

(65) Prior Publication Data
US 2012/0103106 A1    May 3, 2012

(30) Foreign Application Priority Data

Aug. 10, 2009 (CN) .......................... 2009 1 0017811

(51) Int. Cl.
*G01N 3/00* (2006.01)
(52) U.S. Cl.
USPC .......................................................... 73/803

(58) Field of Classification Search
CPC ........................ G01N 3/36; G01N 2203/0044
See application file for complete search history.

(56) References Cited

U.S. PATENT DOCUMENTS 4,502,327 A    3/1985  Scrivener et al.

FOREIGN PATENT DOCUMENTS

| CN | 101240523 A | 8/2008 | |
|---|---|---|---|
| CN | 101387592 A | 3/2009 | |
| CN | 101620050 A | 1/2010 | |
| RU | 2161671 C2 | 1/1998 | |
| RU | 2110368 | * 5/1998 | .............. B23B 25/06 |

* cited by examiner

*Primary Examiner* — Lisa Caputo
*Assistant Examiner* — Brandi N Hopkins
(74) *Attorney, Agent, or Firm* — Michael J. Donohue; Davis Wright Tremaine LLP

(57) ABSTRACT

Disclosed is a gasbag type pavement testing apparatus, comprising a main frame (7), roller wheels (1) and a pneumatic suspension frame system which consists of gasbags (2), ventilated bolts (5), spokes (6), an inflating valve (10), a communicating shaft (11) and rockers (3). The gasbags (2), ventilated bolts (5), spokes (6), inflating valve (10), and communicating shaft (11) constitute an air storing space interconnecting each gasbag, the air storing space is inflated or deflated through the inflating valve (10), and the rockers (3) are hinge-jointed with the spokes (6). The spokes (6), rockers (3) and the communicating shaft (11) constitute a spoke assembly. The roller wheels (1) are driven by the spoke assembly to rotate round the communicating shaft (11), the roller wheels (1) contact the pavement in turn under the joint action of the gasbags (2) and the spoke assembly to simulate the practical situation and hence conduct the rolling test for the pavement. The testing apparatus performs the test with higher accuracy and higher efficiency.

5 Claims, 1 Drawing Sheet

GASBAG TYPE PAVEMENT ACCELERATED LOADING TESTING APPARATUS

This application is the United States National Phase of International Application PCT/CN2010/072322, filed Feb. 2, 2-11. This application also includes a claim of priority to Chinese Application No. 2009/10017811.1 filed Aug. 10, 2009.

CROSS-REFERENCE TO RELATED APPLICATION

This application claims the benefit of Chinese Patent Application No. 2009 10017811.1 filed on Aug. 10, 2009 in the State Intellectual Property Office of China, the disclosure of which is incorporated herein by reference.

BACKGROUND OF THE INVENTION

1. Field of Invention

The present invention relates to the field of the testing apparatus, more particularly, to a ballonet type pavement accelerated loading testing apparatus.

2. Description of the Related Art

A pavement accelerated loading testing apparatus, usually, is a special apparatus for testing, detecting the material and structure of the pavement. Current pavement accelerated loading testing apparatus includes a roller device which typically is a reciprocating roller or a circulating roller. The roller device simulates the practical situation when the vehicles run on the pavement. The conventional testing apparatus applies a roll force by means of a dead weight or hydraulic device, as a result, the conventional testing apparatus is complicated, low efficient, with larger power consumption and often generates a large noise.

SUMMARY OF INVENTION

The present invention has been made to overcome or alleviate at least one aspect of the above mentioned disadvantages. Accordingly, an object of present invention is to provide a pavement accelerated loading testing apparatus which has a higher efficiency and consumes less power while simulating the practical situation more precisely.

According to an aspect of the present invention, there is provided a gasbag type pavement accelerated loading testing apparatus. The testing apparatus comprises a main frame, roller wheels and a pneumatic suspension frame system which consisting of gasbags, ventilated bolts, spokes, an inflating valve, a communicating shaft and rockers. The gasbags, ventilated bolts, spokes, an inflating valve, and a communicating shaft constitute an air storing space interconnecting each gasbag, the air storing space being inflated or deflated through the inflating valve, and the rockers are hinge-jointed with the spokes.

Further, the gasbag is fixed on the spoke by the ventilated bolt at one end, and fixed on the rocker by bolts at the other end; the spokes are welded on the communicating shaft, and the spokes, rockers and the communicating shaft constitute a spoke assembly. The roller wheels are driven by the spoke assembly to rotate round the communicating shaft, and contact the pavement in turn under the joint action of the gasbags and the spoke assembly to conduct the rolling test for the pavement.

Preferably, the spokes are provided in the main frame, the spokes are driven by an electromotor through a belt in shape of V and a reducer.

According to one aspect of present invention, the air storing space of the pneumatic suspension frame system consists of the gasbags, ventilated bolts, spokes, inflating valves, communicating shafts, and the whole air storing space can be inflated and deflated through the inflating valve, whereby the air pressure of the system can be employed to control the rolling force that applied on the testing pavement by the rolling wheel.

According to another aspect of present invention, when one of the rolling wheel rolls the pavement, the rolling force is applied by the compressing gasbag via the hinge-jointed rockers and spokes. The spoke assembly drives the rolling wheels to perform the rolling test.

According to a further aspect of present invention, the spoke assembly is driven by an electromotor through a belt in shape of V and a reducer to rotate round the communicating shaft. The spokes and the rockers of the spoke assembly drive the rolling wheels, which conduct a rolling test in turn under the joint action of the gasbag and the spoke assembly.

With above configuration, the present invention provides at least one of following advantages over the prior art:

firstly, by using the gasbag as the rolling force source, the present invention could simulate more precisely the practical situation when the vehicles run on the pavement with a simple configuration, a higher reliability and a smaller noise;

secondly, the spoke assembly of present invention consists of spokes, rockers and communicating shaft, a plurality of rolling wheels are driven by the spoke assembly to rotate in turn, so as to conduct a rolling test on the pavement under the joint action of the gasbag and the spoke assembly, whereby the efficiency of test is improved with a lower power consumption.

REFERENCE NUMERALS

Figure 1:
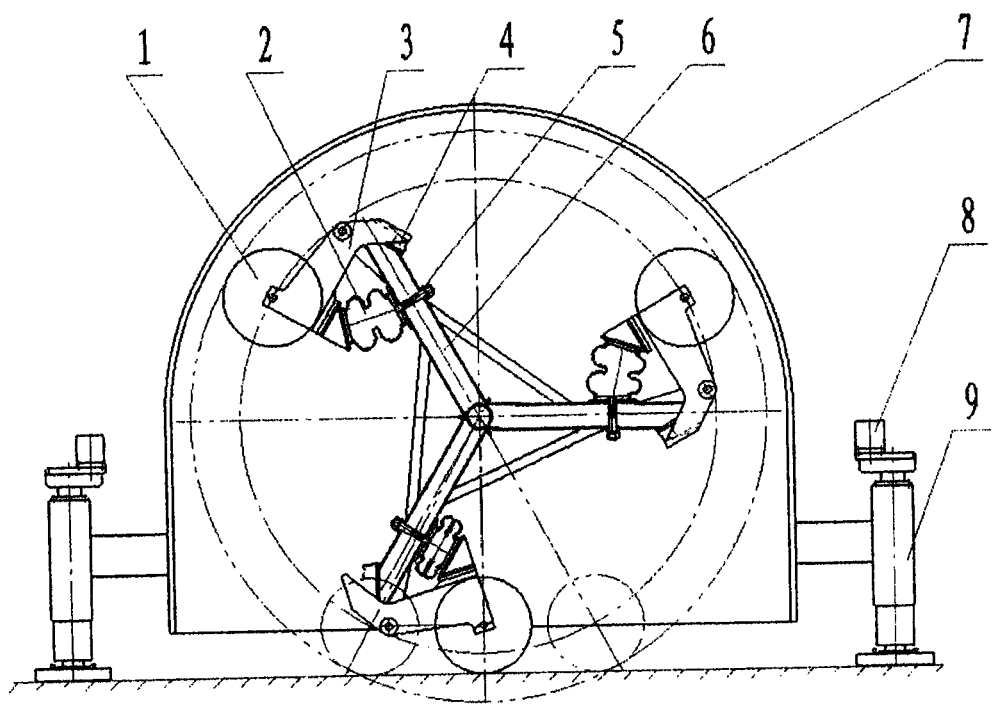
FIG. 1 is a front view of a gasbag type pavement accelerated loading testing apparatus according to present invention.

1—rolling wheel
2—gasbag
3—rocker
4—stopper
5—ventilated bolt
6—spoke
7—main frame
8—step motor
9—supporting leg
10—inflating valve
11—communicating shaft
12—electromotor
13—reducer

DETAILED DESCRIPTION OF PREFERRED EMBODIMENTS

Preferred embodiments of the present invention will be described hereinafter in detail with reference to the attached drawings, wherein the like reference numerals refer to the like elements throughout the specification. These embodiments should not be construed as being limited to the embodiment set forth herein, rather for illustrative purpose.

Figure 2:
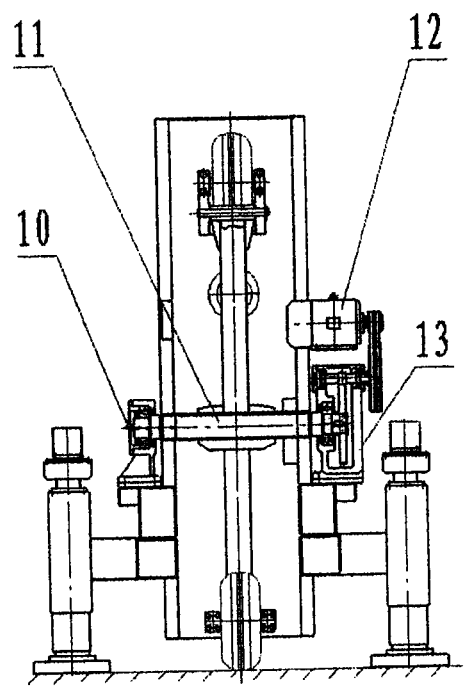
FIG. 2 is a left view of the gasbag type pavement accelerated loading testing apparatus according to present invention.

Referring to FIGS. 1-2, a gasbag type pavement accelerated loading testing apparatus according to present invention comprises a main frame 7, roller wheels 1 and a pneumatic suspension frame system which consists of gasbags 2, ventilated bolts 5, spokes 6, an inflating valve 10, communicating shaft 11 and rockers 3.

The gasbags 2, ventilated bolts 5, spokes 6, inflating valve 10, and communicating shaft 11 constitute an air storing space interconnecting each gasbag. The air storing space is inflated or deflated through the inflating valve 10, the air pressure of the system controls the rolling force applied to the test pavement by the rolling wheel 1.

Via an axle pin, the rocker 3 is hinge-jointed with the spoke 6 in the main frame 7 of the testing apparatus. The spokes 6, rockers 3 and the communicating shaft 11 constitute a spoke assembly. The roller wheels 1 are driven by the spoke assembly to rotate in a clockwise direction, and hence contact the pavement in turn under the joint action of the gasbags 2 and the spoke assembly to conduct the rolling test for the pavement.

According to one aspect of present invention, supporting legs 9 and step motors 8 are provided on the main frame 7 of the testing apparatus. The length of the supporting leg 9 could be adjusted to change the rolling length of the rolling wheel 1 on the pavement. Suppose the air pressure in the air storing space is constant, the length of the supporting leg 9 could be adjusted to change the rolling force that the rolling wheels 1 apply to the pavement. More specifically, the shorter the supporting leg 9 is adjusted to be, the closer the main frame 7 is located to the test pavement, and the bigger the rolling force applied to the pavement becomes.

The gasbag type pavement accelerated loading testing apparatus can be manufactured conveniently and easily according to the drawings. For the purpose of clarity, the well known features involved in present invention are omitted.

Although several exemplary embodiments have been shown and described, it would be appreciated by those skilled in the art that various changes or modifications may be made in these embodiments without departing from the principles and spirit of the disclosure, the scope of which is defined in the appended claims and their equivalents.

The invention claimed is:

1. A gasbag type pavement accelerated loading testing apparatus, comprising
   a main frame (7), roller wheels (1) and a pneumatic suspension frame system which consists of gasbags (2), ventilated bolts (5), spokes (6), an inflating valve (10), a communicating shaft (11) and rockers (3);
   wherein the gasbags (2), ventilated bolts (5), spokes (6), inflating valve (10), and communicating shaft (11) constitute an air storing space interconnecting each gasbag, the air storing space can be inflated or deflated through the inflating valve (10), and the rockers (3) are hinge-jointed with the spokes (6).

2. The gasbag type pavement accelerated loading testing apparatus according to claim 1, wherein
   the gasbag (2) is fixed on the spoke (6) by the ventilated bolts (5) at one end, and fixed on the rocker (3) by bolts at the other end; the spokes (6) are welded on the communicating shaft (11), and the spokes (6), rockers (3) and the communicating shaft (11) constitute a spoke assembly;
   the roller wheels (1) are driven by the spoke assembly to rotate round the communicating shaft (11), the roller wheels contact the pavement in turn under the joint action of the gasbags (2) and the spoke assembly to conduct the rolling test for the pavement.

3. The gasbag type pavement accelerated loading testing apparatus according to claim 2, wherein
   the spokes (6) are provided in the main frame (7), the spokes (6) are driven by an electromotor through a belt in shape of V and a reducer.

4. The ballonet type pavement accelerated loading testing apparatus according to claim 1, further comprising:
   an adjuster which is a supporting leg (9), the length of which could be adjusted to change the rolling length of the roller wheel on the pavement.

5. The gasbag type pavement accelerated loading testing apparatus according to claim 1, further comprising:
   an adjuster which is a supporting leg (9), the length of which could be adjusted to change the rolling force applied on the pavement by the roller wheel.

\* \* \* \* \*